(12) United States Patent
Marmarinos et al.

(10) Patent No.: US 8,334,328 B2
(45) Date of Patent: Dec. 18, 2012

(54) PHOTOPOLYMERIZATION MATERIAL FOR GUMS ISOLATION

(75) Inventors: Vassilios Marmarinos, Artemios (GR); Paschalis Paschalakis, Egaleo (GR)

(73) Assignee: KLOX Technologies Inc., Laval, Quebec (CA)

( * ) Notice: Subject to any disclaimer, the term of this patent is extended or adjusted under 35 U.S.C. 154(b) by 240 days.

(21) Appl. No.: 12/525,890

(22) PCT Filed: Feb. 9, 2007

(86) PCT No.: PCT/GR2007/000006
§ 371 (c)(1),
(2), (4) Date: Mar. 1, 2010

(87) PCT Pub. No.: WO2008/096182
PCT Pub. Date: Aug. 14, 2008

(65) Prior Publication Data
US 2010/0152296 A1 Jun. 17, 2010

(51) Int. Cl.
*G03F 7/029* (2006.01)
*C08F 2/50* (2006.01)
*A01N 31/19* (2006.01)
*A01K 31/185* (2006.01)
*A61C 5/00* (2006.01)

(52) U.S. Cl. ............ 522/48; 522/36; 514/576; 514/605; 514/729; 433/217.1

(58) Field of Classification Search .................... 522/36, 522/48; 514/576, 605, 729; 433/136, 138, 433/217.1, 137, 139, 140, 214, 40; 424/53
See application file for complete search history.

(56) References Cited

U.S. PATENT DOCUMENTS

| | | | | |
|---|---|---|---|---|
| 4,846,165 A | * | 7/1989 | Hare et al. | 228/156 |
| 5,977,199 A | * | 11/1999 | Xie | 522/8 |
| 6,423,697 B1 | * | 7/2002 | Friedman | 514/164 |
| 2002/0197214 A1 | | 12/2002 | Bublewitz et al. | |
| 2003/0134932 A1 | | 7/2003 | Lehmann et al. | |
| 2003/0162760 A1 | * | 8/2003 | Masatsuji et al. | 514/184 |
| 2004/0028624 A1 | | 2/2004 | Bublewitz et al. | |
| 2004/0097627 A1 | | 5/2004 | Vallittu et al. | |
| 2005/0100514 A1 | * | 5/2005 | Sakaguchi et al. | 424/53 |
| 2005/0124721 A1 | | 6/2005 | Arthur et al. | |
| 2005/0124722 A1 | | 6/2005 | Arthur et al. | |
| 2005/0249677 A1 | | 11/2005 | Malcmacher et al. | |
| 2007/0148623 A1 | * | 6/2007 | Dias et al. | 433/223 |

FOREIGN PATENT DOCUMENTS

| | | | |
|---|---|---|---|
| EP | 0356868 | * | 3/1990 |
| WO | WO9836700 | | 8/1998 |
| WO | WO02087642 | | 11/2002 |
| WO | WO2004073540 | | 9/2004 |

* cited by examiner

Primary Examiner — Michael Pepitone
Assistant Examiner — Jessica Paul
(74) Attorney, Agent, or Firm — Ropes & Gray LLP

(57) ABSTRACT

The main goal of the present invention is the development of a polymerizable material for isolation and protection of the gums and generally the soft tissues of the oral cavity. For better protection during various procedures of the dental surfaces. The composition of the material can contain many other substances that strengthen its qualities and protective action. Such substances can be various substances that have antioxidative, sedative, anti-inflammatory, analgesic, anti-irritant action etc.

9 Claims, No Drawings

US 8,334,328 B2

PHOTOPOLYMERIZATION MATERIAL FOR GUMS ISOLATION

CROSS-REFERENCE TO RELATED APPLICATIONS

This application is the U.S. national phase of International Application No. PCT/GR2007/000006 filed 9 Feb. 2007, the entire contents of which are hereby incorporated by reference.

BACKGROUND

Until today the usual methods of teeth whitening, were based on the use of various peroxides like hydrogen peroxide or carbamide peroxide, which when combined with other inert raw materials give various types of products such as gels, solutions, films etc. These products are applied either directly on the teeth or by using special made cases in order to fit the teeth which will be whitened. The content of these products in peroxide varies on whether the whitening will be made by the dentist or at home by the patient after the dentist's directions. The whitening products which are made for use at home by the patient, contain less peroxide, in order to reduce the danger of burns and wounds on the gums in the event of improper use. Conversely, the products which will be used directly by the dentist, have high concentration of peroxides that can reach 40% by weight of the product. This increases the danger of gum wounds when using the teeth whitening material. In these cases the use of a material that will protect and isolate the patient's gums from the action of peroxides is needed.

The known materials which were used until today for the isolation and protection of the gums, although they offer protection, do not secure the patients health. Accidents often occur during the whitening or other dental procedure which make impractical to continue and sometimes the patient can be injured.

For example, the rubber gum isolators are unmanageable and do not secure the impermeability of the materials which will be used on the teeth, as they don't fit strictly on the gums. Besides, quite often they bother the patient either from false adjustment or by eventual heating when laser is used.

Moreover, there are various photopolymerized substratums which have their defects. Usually, these materials are hydrophobic, therefore in certain cases their capability to remain on the soft tissues is affected, while in others in order to increase their bonding capacity, additives which lead to intense polymerization are used, resulting in removal difficulty. The intense polymerization of these materials increases the temperature which in some cases is important as the polymerization reaction is exothermic. This results in the burning of patient's gums where the use of these materials has been made.

Finally, none of the materials for the isolation and protection of the gums, which were used until today, contain other substances for the protection of the gums which can prevent for example the peroxide teeth whitening material from burning and wounding the gums when not used properly.

This invention presents a photopolymerized material for the isolation of the gums which contains known anti-oxidant substances, that prevent the oxidative peroxides, the teeth whitening products contain, which can damage the gums. Therefore, when polymerized all these materials can congeal very quickly with the use of light radiant energy, making a durable substratum which can firm the gums and can be easily removed after the procedure has been concluded. On the other side it does not overheat during congealment, causing burning and pain to the patient's gums.

SUMMARY AND OBJECTS OF THE INVENTION

The main goal of the present invention is the development of a material for isolation and protection of the gums and generally the soft tissues of the oral cavity, for better protection during various procedures on the dental surfaces.

The present invention gives compositions that can be easily and quickly applied, with accuracy on the tissues that must be protected and isolated. They develop a barrier which has the required hardness and adhesion with the tissues, for the effective prevention of various agents who affect these sensitive tissues. It has also the advantage of easily being removed, after the procedure is over, without deposits. All the compositions that have been chosen have a low speed of polymerization in order to reduce the discomfort of the patient and damage of the tissues from the heat that is produced during polymerization.

There are many monomers that can be part of the compositions of the present invention either alone or among other compositions.

In the present invention the barrier is accomplished by the incorporation, in the composition of the material, of at least one monomer which is preferably of low toxicity. The monomer can be either the chemical clear form of at least one monomer or a mixture of various monomers that depends from the application of the photopolymerization material.

In the composition an activator is incorporated which inducts the link of the monomer when the material is exposed to appropriate light radiant energy. The activator has been chosen because of its low toxicity and its compatibility with the other substances that contain the composition of the material.

The composition of the material which isolates and protects the gums or the soft tissues of the oral cavity can contain many other substances that strengthen its qualities and protective action. Such substances can be various compounds that have antioxidant action, which can be very beneficial when used to offer protection from materials with oxidative actions like peroxides. They can also be substances which have sedative, anti-inflammatory, analgesic, anti-irritant action etc., for extra protection of the gums because they can develop such circumstances when applied on the dental surfaces. The incorporation of these substances in the composition of the protective material, apart from the immediate protection of the gums it offers, can also result in the reduction of the heat that is released, during the polymerization of the material, so patient's discomfort and burning, during the application, is avoided.

DETAILED DESCRIPTION OF THE INVENTION

The photopolymerized material of isolation and protection of the gums of the present invention is applied to many dental procedures that require protection of the soft tissues from the action of oxidative or corrosive agents. The composition of the material of the present invention includes at least one monomer, an activator to initiate the reaction of polymerization and at least one of the following ingredients: one or more substances with anti oxidative action, one or more chemical or plant substances with anti-inflammatory, sedative or anti-irritant action and one or more inert ingredients as well.

The material can be photopolymerized after its application to the gums with any light radiant energy using the full electromagnetic spectrum.

A. Monomers

The said photopolymerized material that aims to protect the gums can contain one monomer or a mixture of monomers according to the purpose the material will be used for. Their selection depends on the situation from which we need to protect the gums. Generally, it is preferably selected for its substantially low toxicity to patients.

Some examples of monomers that are convenient for the present invention are the following: Alkylmethacrylates, alkylhydroxymethacrylates, alkyl-aminomethacrylates and derivatives thereof. The alkylmethacrylates include triethylene glycol dimethacrylate, polyethylene glycol (PEG) dimethacrylate (all molecular weights), butane di-ol dimethacrylate, and equivalents. The alkylhydroxymethacrylates include 2-hydroxy ethyl methacrylate, glycerol dimethacrylate, bis-GMA, and equivalents. The alkylaminomethacrylates include urethane dimethacrylate and equivalents.

The concentration of the monomer in the material composition of the present invention can range from 40% to 99%, preferably from about 50% to about 95% and most preferably from about 60% to about 90% by weight of the composition. The convenient monomers are the "alkylaminomethacrylates". The most convenient is the "Diurethane Dimethacrylate" or mixture of its monomers.

B. Activator

The activators of the polymerization are substances that lead to the cross-linking of the monomers when the material is exposed to appropriate light radiant energy. The activators can be photoinitiators and amine type additives as required.

Examples of photoinitiators (without being the only ones) include camphorquinone, benzyl, diacetyl, benzoin methyl ether, isopropyl ether, benzoin isobutyl ether, 2-hydroxy-2-methyl-1-phenyl-1-propanone, diphenyl 2,4,6-trimethylbenzoyl phosphine oxide, benzoin ethyl ether, benzophenone, 9,10-anthraquinone, and equivalents.

Various additives can be incorporated optionally in the material, in order to reinforce the action of the activator.

Examples of amine type additives include dimethyl amino ethyl methacrylate, tri ethyl amine, 2-dimethylamino ethanol, diethyl amino ethyl methacrylate, trihexyl amine, N,N-dimethyl-p-toluidine; N-methylethanolamine, and equivalents.

The activator of the photopolymerized material of the present invention can participate from about 0.01% to about 5%, preferably from about 0.1% to about 3%, more preferably from about 0.5% to about 2% by weight of the composition. The preferred activator includes camphorquinone.

C. Antioxidant Substances

These substances are incorporated in the said photopolymerized material of insulating the gums, in order to increase the protection of the said material, when the substances are used, display oxidative action like hydrogen peroxide or urea peroxide. The presence of substances with antioxidative action are opposed to the oxidative action of the oxidants that come in contact with the gums, in the case that the adjustment of the said material is not proper in order to fully cover them. Examples of substances with antioxidant action which can be incorporated in the material of the present invention, without excluding others are Vitamin E, Butylated Hydroxyanisole, Butylated Hydroxytoluene, green tea, honey.

The said antioxidant substances of the present invention are provided in a proportion, when included, from about 0.1% to about 40%, preferably from 0.5% to about 35% and more preferably from about 1% to about 30% by weight of the composition. The preferred antioxidative substance is Vitamin E.

D. Substances with Anti-Inflammatory or Sedative Action

These substances are incorporated in the said photopolymerized material of the invention in order to reduce the inflammation, the irritation or the pain of the patient, who will undergo a dental procedure with materials which can worsen the situation or cause problems on the gums.

Examples of substances with anti-inflammatory or sedative action which can be incorporated in the material of the present invention, without excluding others, are a-bisabolol, d-panthenol, substances or mixtures from various plants such as chamomile and aloe vera, or pharmaceutical substances that display such action like ibuprofen and nimesulide which can also be incorporated.

These substances of the present invention are provided in a proportion, when included from about 0.01% to about 10%, preferably from about 0.1% to about 8% by weight of the composition. The preferred is chamomile oil, a-bisabolol and Ibuprofen.

Methods of Use

The inventive polymerizable isolation barrier material of the present invention is prepared in the form of paste or gel that is rheologically able to be applied with the aid of a suitable syringe and to remain to the gums, until the polymerization by appropriate light radiant energy is completed. Furthermore, depending on its application the material can be prepared also in the form of an emulsion, dispersion, suspension, solution etc. The said photopolymerizable material can be prepared in the form of strip or paste which will be placed on the area of the gums that needs isolation, by using the fingers. After being properly formed on the gums it will be polymerized by suitable light radiant energy.

EXAMPLES

Several examples of the present invention follow, without excluding any other example that would emerge from any of the raw material that are mentioned above for the preparation of the inventive protective gums barrier.

Example 1

| COMPONENT | PERCENT BY WEIGHT OF THE MIXTURE |
|---|---|
| Diurethane Dimethacrylate mixture of isomers | 67.35 |
| Silica | 6.00 |
| Tocopheryl Acetate | 25.00 |
| Blue pigment | 0.15 |
| DL-Camphorquinone | 1.50 |

This example gives the composition of a protective and insulating material of the gums which can be used during the teeth whitening procedure with material which contains oxidative and irritant substances, such as peroxides or acids. The presence of Vitamin E increases the protection that the material will offer to the gums against peroxides that maybe reach the gums. It also reduces the speed of the polymerization reaction and thus the heat released.

Example 2

| COMPONENT | PERCENT BY WEIGHT OF THE MIXTURE |
|---|---|
| Diurethane Dimethacrylate mixture of isomers | 67.05 |
| Triehylene Glycol Dimethacrylate 95% | 10.00 |
| Silica | 6.00 |
| Tocopheryl Acetate | 15.00 |
| Titanium oxide | 0.30 |
| Blue pigment | 0.15 |
| DL- Camphorquinone | 1.50 |

The presence of Vitamin E increases the protection that the material will offer to the gums against peroxides that may reach the gums. It also reduces the speed of the polymerization reaction and thus the heat released.

Example 3

| COMPONENT | PERCENT BY WEIGHT OF THE MIXTURE |
|---|---|
| Diurethane Dimethacrylate mixture of isomers | 88.50 |
| Silica | 7.00 |
| Chomomile Oil | 2.00 |
| A-Bisabolol | 0.30 |
| Titanium oxide | 0.30 |
| Blue pigment | 0.15 |
| DL- Camphorquinone | 1.75 |

The presence of chamomile oil and A-bisabolol add anti-inflammatory properties to the insulating material, in case irritant substances reach to the gums.

Example 4

| COMPONENT | PERCENT BY WEIGHT OF THE MIXTURE |
|---|---|
| Diurethane Dimethacrylate mixture of isomers | 74.50 |
| Triehylene Glycol Dimethacrylate 95% | 5.00 |
| Silica | 6.00 |
| Tocopheryl Acetate | 10.00 |
| Chomomile Oil | 2.00 |
| A-Bisabolol | 0.30 |
| Titanium oxide | 0.30 |
| Blue pigment | 0.15 |
| DL- Camphorquinone | 1.75 |

The presence of Vitamin E increases the protection that the material will offer to the gums against peroxides that may reach the gums. It also reduces the speed of the polymerization and thus the heat released. The presence of chamomile oil and A-bisabolol add anti-inflammatory properties to the material, in case irritant substances reach to the gums.

The invention is reflected by the appended claims.

The invention claimed is:

1. A polymerizable isolation barrier for the isolation and protection of the gums during various dental procedures which is a mixture comprising:
    40% to about 99% of urethane dimethacrylate by weight of barrier;
    at least one activator to activate the diurethane dimethacrylate, wherein the activator comprises from about 0.01% to about 5% of camphorquinone or 9,10-anthraquinone by weight of barrier;
    10% to 25% vitamin E by weight of barrier; and
    at least one filler, wherein the at least one filler includes silica.

2. The polymerizable isolation barrier according to claim 1, further comprising at least one inert raw material.

3. The polymerizable isolation barrier according to claim 2, wherein the at least one inert raw material is selected from the group consisting of polymerization initiators, polymerization activators, stabilizers, UV light absorbers, colorants, therapeutic agents, flavoring agents and viscosity/rheological modifiers.

4. The polymerizable isolation barrier according to claim 1, further comprising at least one substance which has anti-inflammatory action.

5. The polymerizable isolation barrier according to claim 4, wherein the at least one substance that has anti-inflammatory activity includes at least one of a-bisabolol, chamomile oil, aloe vera and d-panthenol.

6. The polymerizable isolation barrier according to claim 4, wherein the at least one substance which has anti-inflammatory action is included in a concentration from about 0.01% to about 10% by weight of barrier.

7. The polymerizable isolation barrier according to claim 1, further comprising at least one substance which has sedative action.

8. The polymerizable isolation barrier according to claim 7, wherein the at least one substance that has sedative activity includes at least one of ibuprofen and nimesulide.

9. The polymerizable isolation barrier according to claim 7, wherein the at least one substance that has sedative activity is included in a concentration from about 0.01% to about 10% by weight of barrier.

* * * * *